(12) United States Patent
Harms et al.

(10) Patent No.: US 8,888,742 B2
(45) Date of Patent: Nov. 18, 2014

(54) PROTECTIVE SHIELD FOR HYPODERMIC SYRINGE

(75) Inventors: Volker Harms, Kassel (DE); Markus Kaemereit, Nottuln (DE)

(73) Assignee: B. Braun Melsungen AG, Melsungen (DE)

( * ) Notice: Subject to any disclaimer, the term of this patent is extended or adjusted under 35 U.S.C. 154(b) by 768 days.

(21) Appl. No.: 13/129,799

(22) PCT Filed: Nov. 2, 2009

(86) PCT No.: PCT/US2009/062986
§ 371 (c)(1),
(2), (4) Date: Aug. 3, 2011

(87) PCT Pub. No.: WO2010/059415
PCT Pub. Date: May 27, 2010

(65) Prior Publication Data
US 2011/0282296 A1    Nov. 17, 2011

Related U.S. Application Data

(60) Provisional application No. 61/115,673, filed on Nov. 18, 2008.

(51) Int. Cl.
*A61M 5/00* (2006.01)
*A61M 5/32* (2006.01)

(52) U.S. Cl.
CPC ........... *A61M 5/3216* (2013.01); *A61M 5/3213* (2013.01)
USPC ......................................... 604/110; 604/198

(58) Field of Classification Search
CPC . A61M 5/2305; A61M 5/321; A61M 5/3213; A61M 5/3216; A61M 5/3219; A61M 2005/3217
USPC .................. 604/192, 263, 110, 111, 197, 198
See application file for complete search history.

(56) References Cited

U.S. PATENT DOCUMENTS

| 5,599,313 | A | * | 2/1997 | Gyure et al. | .................. 604/192 |
| 5,599,318 | A |   | 2/1997 | Sweeney et al. | |
| 5,632,732 | A | * | 5/1997 | Szabo et al. | .................. 604/192 |

(Continued)

FOREIGN PATENT DOCUMENTS

| EP | 0812597 | 12/1997 |
| EP | 1743668 | 7/2005 |

OTHER PUBLICATIONS

International Search Report completed Jul. 9, 2010 and mailed Jul. 12, 2010 from corresponding International Application No. PCT/US2009/062986; Filed Nov. 2, 2009 (5 pages).

(Continued)

*Primary Examiner* — Kami A Bosworth
*Assistant Examiner* — Glen Janson
(74) *Attorney, Agent, or Firm* — Klein, O'Neill & Singh, LLP (57) ABSTRACT

A protective cap coupled to a syringe having a needle attached thereto. The protective cap may be pivoted to a position in alignment with the needle so that the protective cap substantially envelops the needle. A plug may be inserted into the cap to envelop or capture the needle within a hollow body of the plug to secure at least a tip of the needle.

14 Claims, 5 Drawing Sheets

(56) References Cited

U.S. PATENT DOCUMENTS

| | | | |
|---|---|---|---|
| 5,665,075 A * | 9/1997 | Gyure et al. | 604/263 |
| 5,792,121 A | 8/1998 | Tamaro | |
| 6,645,182 B1 * | 11/2003 | Szabo | 604/192 |
| 2002/0151852 A1 | 10/2002 | Crawford et al. | |
| 2006/0270979 A1 | 11/2006 | Simas, Jr. et al. | |
| 2008/0269693 A1 | 10/2008 | Steube et al. | |
| 2010/0049141 A1 * | 2/2010 | Gardner | 604/192 |

OTHER PUBLICATIONS

Written Opinion completed Jul. 9, 2010 and mailed Jul. 12, 2010 from corresponding International Application No. PCT/US2009/062986; Filed Nov. 2, 2009 (3 pages).

European Search Report on related European Application No. 09 827 992.0 from the European Patent Office (EPO) dated Apr. 1, 2014.

* cited by examiner

PROTECTIVE SHIELD FOR HYPODERMIC SYRINGE

CROSS-REFERENCE TO RELATED APPLICATIONS

This application is a national phase application of International Application No. PCT/US2009/062986, filed Nov. 2, 2009, entitled PROTECTIVE SHIELD FOR A HYPODERMIC SYRINGE, which claims the benefit of U.S. Provisional Application No. 61/115,673, filed Nov. 18, 2008, the contents of which are expressly incorporated herein by reference.

FIELD OF ART

The disclosure relates generally to caps for a needle device, and more particularly, to hinged cap devices for use with hypodermic needles.

BACKGROUND

Recapping the needle of a syringe is a common procedure practiced by healthcare providers. The recapping procedure may occasionally cause "needle sticks" since healthcare providers sometimes misalign needles with the openings of the caps, or inadvertently stick themselves while handling the syringe. Typically, healthcare providers need to be protected from needle sticks between drawing up fluids into the syringe and administering injections through the needle since fluids linked to these "clean" type of needle sticks may cause injuries and adverse reactions. Also, healthcare providers need to be protected from contracting contagious diseases that may be carried by contaminated needles, since it has been well recognized that no contact should be made with a contaminated needle.

In an effort to reduce or eliminate needle stick injuries, it was necessary to improve the state of the art. The improvements minimize or eliminate the clean type and, the more dangerous, contaminated type of needle stick injuries.

SUMMARY

The embodiments of the present invention have several features, no single one of which is solely responsible for their desirable attributes. Without limiting the scope of the present embodiments as expressed by the claims that follow, their more prominent features now will be discussed briefly.

The present invention includes a protective cap that may be coupled to a syringe having a needle attached thereto. The protective cap may be pivoted to a position in alignment with the needle so that the protective cap substantially envelops the needle. This feature may protect the healthcare provider from needle sticks between drawing up fluids into the syringe and administering injections.

A second feature of the present invention helps to protect healthcare providers from contracting contagious diseases by providing a plug that may be inserted into the cap to envelop, capture or trap the needle to secure at least the tip of the needle. This enhanced safety feature further decreases the possibility of the user or bystanders from being exposed to the tip of the contaminated needle.

In one aspect, a protective shield is provided for protecting a needle coupled to a syringe. The protective shield includes a coupling member for connecting to a syringe. The shield also includes a cap, which defines a recessed space and is hinged to the coupling member. The cap is displaceable with respect to the syringe to a first position aligned with a longitudinal centerline of the syringe and a second position non-aligned with the longitudinal centerline of the syringe. A plug is movably insertable into the recessed space of the cap.

In another aspect, a protective shield is provided which includes a cap defining a recessed space and having a coupling member for connecting to a syringe having a needle. The cap is displaceable with respect to the needle to a first position having the needle disposed within the recessed space and a second position having the needle outside the recessed space. The protective shield also includes a plug having a hollow tubular body including an open end. The plug is displaceable with respect to the cap to envelop the needle within the hollow tubular body though the open end when the cap is in the first position.

In yet another aspect, a method is provided for shielding a needle coupled to a syringe. The method includes moving a cap defining a cavity from an open position where the needle is outside the cavity to a closed position where the needle is substantially within the cavity; moving a plug having a hollow tubular body including an open end into the cavity; and receiving the needle within the hollow tubular body though the open end.

As discussed below, the hinged protective shield allows the healthcare provider to safely cover a sharp needle tip during the periods between drawing up fluids and administering an injection to a patient, or immediately after injecting the patient. The needle may be temporarily shielded without locking the shield to allow the needle to be exposed when necessary. Before the healthcare provider discards the syringe, such as after use, he or she can manipulate the hinged protective shield into a substantially secure position so the syringe can no longer be used or the needle exposed to cause needle stick injuries.

In a still further aspect of the present invention, a protective shield for covering a needle having a sharp tip is provided. The protective shield comprising a coupling member, a cap defining a recessed space along a lengthwise axis and hinged to the coupling member, the cap being pivotable relative to the coupling member from a first position aligned with a longitudinal centerline of a needle and a second position non-aligned with the longitudinal centerline of the needle; and a plug movably insertable into the recessed space of the cap.

In yet another aspect of the present invention, a protective shield comprising a cap defining a recessed space, an axial opening, and having a coupling member for connecting to a syringe having a needle is provided. The cap being displaceable to an open position where the recessed space is not occupied by the needle and a ready position where the needle occupies a portion of the recessed space; and a plug having a hollow tubular body including an open end, the plug being displaceable through the axial opening of the cap to a secured position with respect to the cap to receive the needle through the open end of the plug when the cap is in the ready position.

In a still further aspect of the present invention, a method for manufacturing a protective shield to shield a needle coupled to a syringe is provided. The method comprising attaching a coupling member to a needle hub, said needle hub having a needle mounted thereto and said coupling member comprising a living hinge; forming a cap comprising two side walls defining a cavity and an open axial end at a distal end of the cap, said cavity sized to receive a needle when said cap is aligned with said needle; inserting a plug comprising an open proximal end and a closed distal end into the open axial end of the cap and engaging an exterior teeth on the plug with the cap to delimit distal of movement of the plug relative to the cap; and wherein the plug is insertable, at least in part, into the cavity of the cap.

In still yet another aspect of the invention, a protective shield assembly for protecting a needle is provided. The protective shield assembly comprising a hub having a needle attached thereto and a cap hingedly connected to the hub; wherein the cap comprises wall surfaces defining a space for receiving the needle in a secured position.

This brief summary has been provided so that the nature of the invention may be understood quickly. A more complete understanding of the invention can be obtained by reference to the following detailed description of the embodiments thereof concerning the attached drawings.

BRIEF DESCRIPTION OF THE DRAWINGS

Embodiments of the present invention now will be discussed in detail with an emphasis on highlighting the advantageous features. These embodiments depict the novel and non-obvious aspects of the invention shown in the accompanying drawings, which are for illustrative purposes only. These drawings include the following figures, in which like numerals indicate like parts.

DETAILED DESCRIPTION

The detailed description set forth below in connection with the appended drawings is intended as a description of exemplary embodiments of a hinged cap assembly for use with needles having sharp needle tips provided in accordance with aspects of the present invention and is not intended to represent the only forms in which the present invention may be constructed or used. The description sets forth the features and the steps for using the hinged cap assembly of the present invention in connection with the illustrated embodiments. It is to be understood that the same or equivalent functions and structures may be accomplished by different embodiments and are also intended to be encompassed within the spirit and scope of the present invention, especially those incorporating a combination of features shown in the different embodiments included herein.

Figure 1:
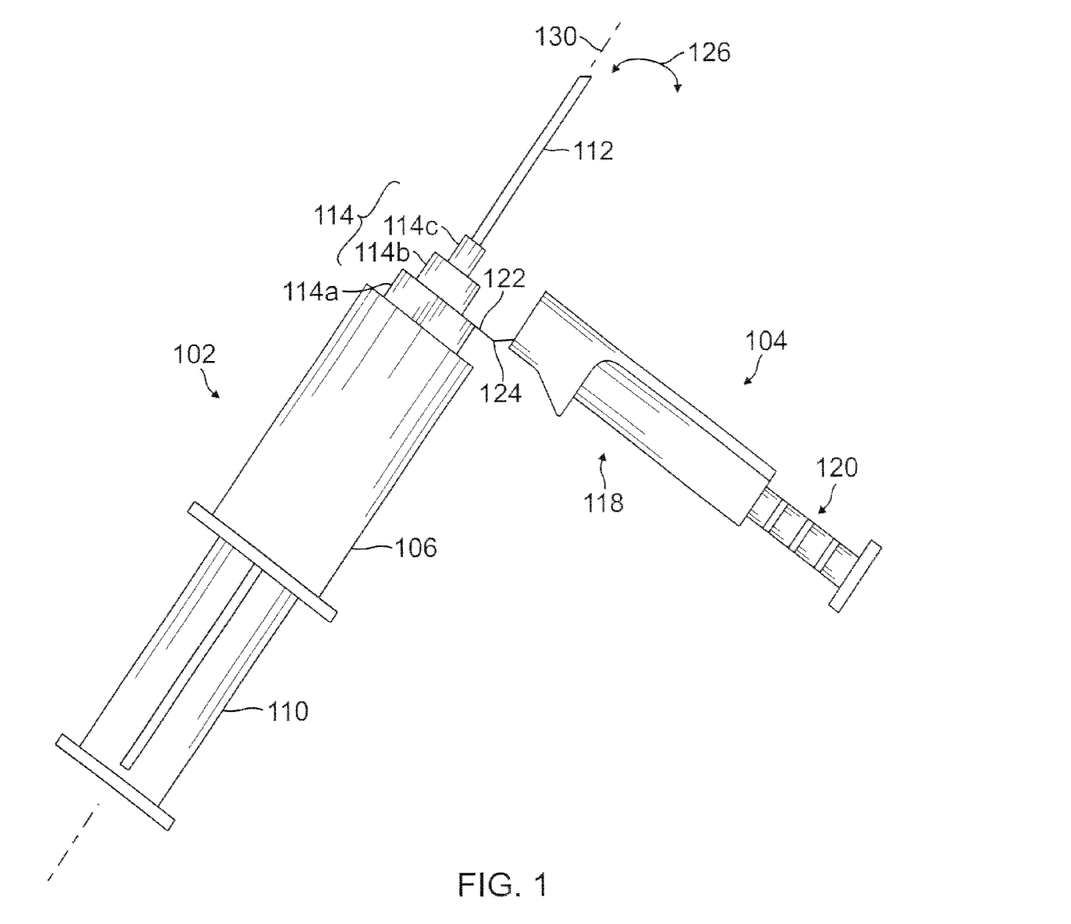
FIG. 1 is a perspective view of a hypodermic syringe coupled to a protective shield in accordance with an embodiment of the present invention.

FIG. 1 is a perspective view of a standard hypodermic syringe 102 coupled to a protective hinged cap assembly 104 (hereinafter "shield 104") provided in accordance with an embodiment of the present invention. As shown in FIG. 1, generally, hypodermic syringe 102 includes a body portion or syringe barrel 106 configured to receive a plunger 110 at one end and includes a hypodermic needle 112 coupled at the opposite end or discharge end.

Figure 5A:
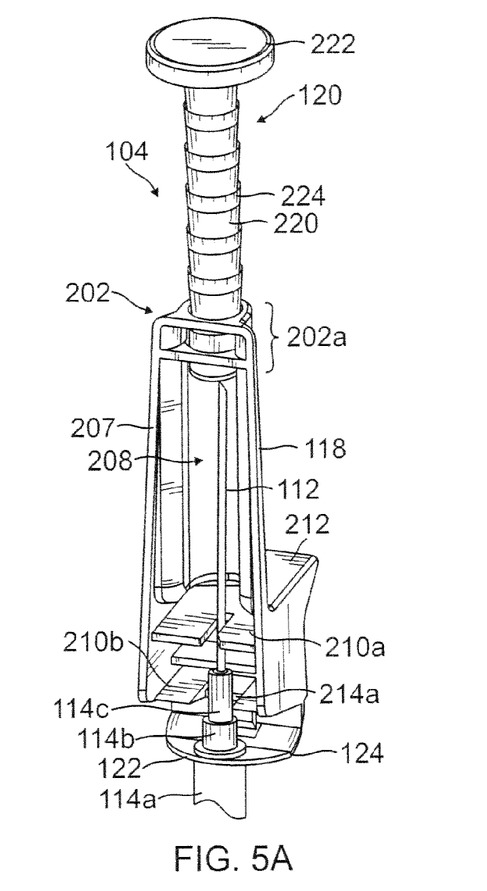
FIGS. 5A and 5B are simplified illustrations of the operation of the shield in accordance with an embodiment of the present invention.
Figure 5B:
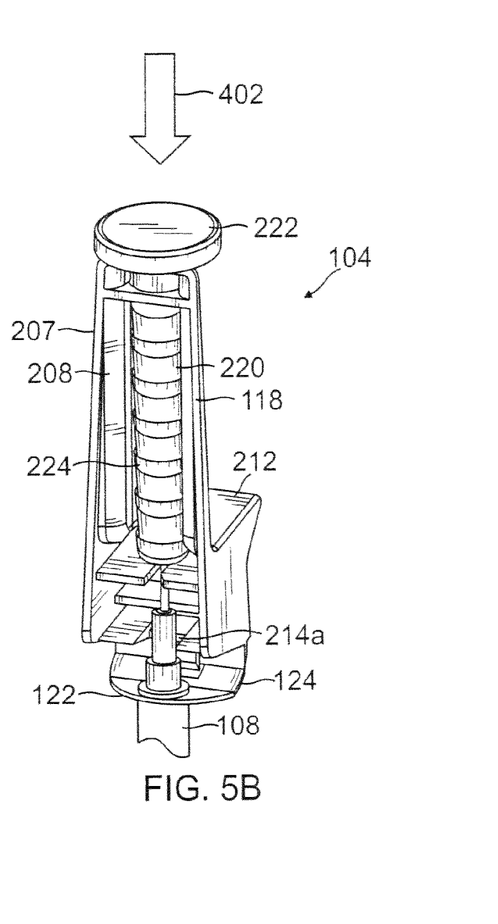

Generally, shield 104 includes a coupling member 122 for mounting a cap 118, which defines an interior cavity therein for shielding needle 112 preceding or following an injection and a plug 120. Cap 118 and plug 120 may be made by injection molding or similarly known procedures. As will be described in more detail below, shield 104 is rotatable or pivotable with respect to coupling member 122 from between a packaged or ready position (FIG. 5A) to an open position (FIG. 1) and from the ready position to a secured position (FIG. 5B).

In one embodiment, needle 112 is attached to a needle hub 114b which is attached to a male luer tip (not shown) of syringe barrel 106, which is surrounded by a threaded collar 114a, as is well known in the art. An integral coaxial cylindrical needle hub 114c extends distally from needle hub 114b for securing needle 112 to the needle hub 114b. Needle hub 114c is dimensioned with a smaller diameter than needle hub 114b and is adapted to be received by a needle alignment mechanism when shield 104 is in the ready position and in the secured position, as described in more detail below. In a preferred embodiment, the needle hub 114c and the needle hub 114b are unitarily formed. In an alternative embodiment, the needle hub 114c and needle hub 114b may be integrally or unitarily formed to the coupling member 122 and made part of the shield 104.

Figure 2A:
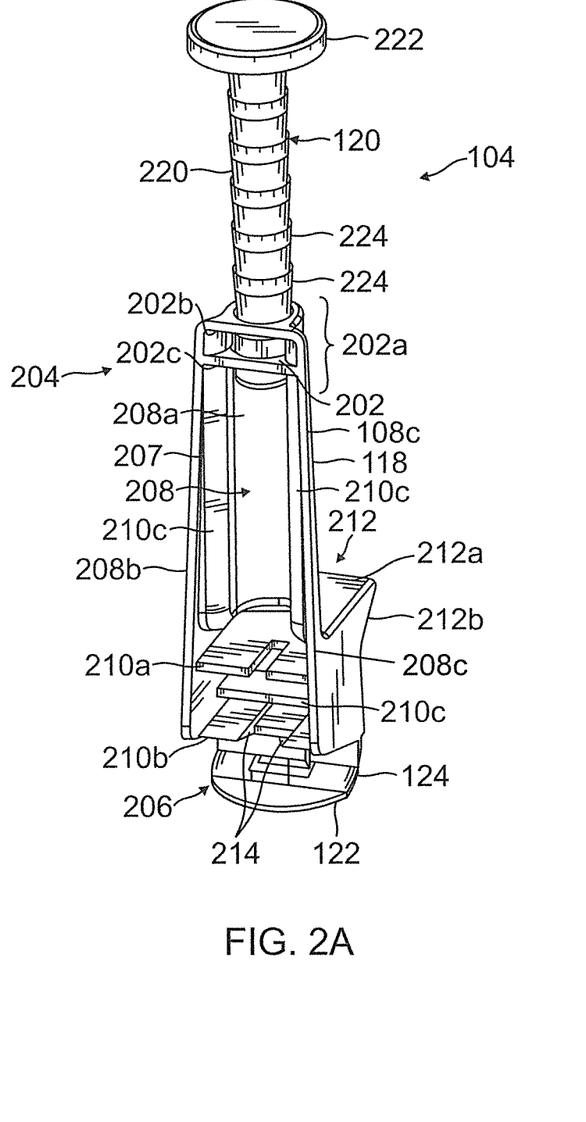
FIG. 2A is a front perspective view of the protective shield in accordance with an embodiment of the present invention.

In one embodiment, shield 104 includes a cap 118 formed in a telescoping arrangement with a plug 120. Referring to FIG. 2A, cap 118 generally is configured to shield and contain needle 112 in the ready and secured positions, to be easily manipulated between the ready and open positions; and to be easily manipulated between the open and secured positions. Cap 118 includes a base wall 208a and two side walls 208b and 208c, defining a generally U-shaped or otherwise open cavity or recessed space 208 therebetween, also known as a channel. Recessed space 208 is configured and dimensioned to have an internal clearance sized and shaped to allow a needle of a given length to pass unobstructed when cap 118 is pivoted to substantially align and envelop needle 112.

Base wall 208a substantially follows the contour of the profile and serves to support various components of cap 118, as described in more detail below. The side walls 208b, 208c extend upward, generally orthogonally, from base wall 208a and are generally parallel to each other. An end section 202 extends between the two side walls 208b, 208c at distal end 204 of cap 118. In one embodiment, a passageway 202a is defined through two spaced apart end plates 202b and 202c formed at end section 202 of cap 118. Passageway 202a may be sized and shaped to receive plug 120 and provide a stable passage for passing plug 120 therethrough. Stability is facilitated by incorporating openings sized to support plug 120 at the two spaced apart end plates 202b. 202c locations. Passageway 202a provides access through distal end section 202 to recessed space 208. Thus, insertion of plug 120 into passageway 202a allows at least the proximal end of plug 120 to enter recessed space 208. In this manner, plug 120 and cap 118 operate in a telescoping arrangement.

Figure 2B:
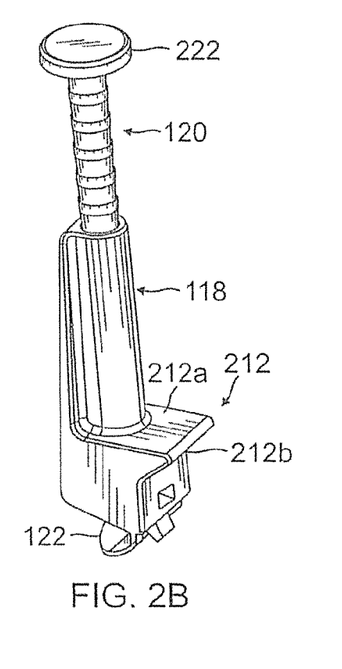
FIG. 2B is a rear perspective view of the protective shield in accordance with an embodiment of the present invention.

With reference again to FIG. 2A and now to FIG. 2B, in one exemplary embodiment, recessed space 208 incorporates a first needle alignment mechanism 210a for aligning needle 112 within cap 118, the first needle alignment mechanism 210a being located within proximal end 206 of cap 118. The first needle alignment mechanism 210a includes a wall extending perpendicularly from each side wall 208b, 208c and having a gap, channel, or slot formed thereon adapted to receive needle 112 to align it relative to the longitudinal axis of cap 118. The entrance to the gap of the first needle alignment mechanism 210a may include a sloped leading edge for directing the needle 112 into the gap of the first needle alignment mechanism 210a when cap 118 is rotated from the open position to the ready position.

In another exemplary embodiment, a second needle alignment mechanism 210b may be incorporated into cap 118 for aligning needle 112 with cap 118. Second needle alignment mechanism 210b is a wall extending perpendicularly to side walls 208b, 208c and having a gap or slot formed thereon having a sloped leading edge. The gap is dimensioned to receive needle hub 114c, and therefore may be wider than the gap of the first needle alignment mechanisms 210a, and is located proximal thereof.

In some embodiments, structural support member 210c is disposed within cap 118 to provide structural support to cap 118. Structural support member 210c include the appropriate clearances, slots, openings, recesses, channels and the like to unobstructively receive and accommodate needle 112 when cap 118 is pivoted to substantially align and envelop needle 112. It should be understood that structural support member 210c may be any type of support structures, such as ribs, shelves and the like, that may be formed in any number of structural arrangements suited to provide mechanical support to cap 118, to accommodate all forces applied thereto. In the embodiment shown, structural support member 210c also serves as a needle stop for stopping over-rotation of the cap relative to the needle shaft, as shown in FIG. 5A, by abutting the base of the needle.

In some instances, a healthcare provider may desire to hold cap 118 in a position aligned with needle 112, for example, in the as packaged or in the ready positions, but prior to actual use of the syringe on a patient, such as following aspiration of medicament into the syringe. In one embodiment, cap 118 may include a retaining means 214 for temporarily holding cap 118 in the ready position relative to needle 112. Retaining means 214 may include any suitable means for temporarily retaining needle in the ready position. In one exemplary embodiment, a pair of détentes, such as rounded members, fingers or other projections may be positioned in cap 118 to hold needle 112 in a temporarily fixed position within recessed space 208. For example, as needle 112 is received into recessed space 208, projections 214a may be brought in line with corresponding recesses disposed on needle hub 114c of needle 112, such that, projections 214a fall partially into the recesses, thus, holding needle 112 temporarily in position. Alternatively, friction may be used between projections 214a and needle hub 114c to hold needle 112 in position.

To open the cap 118 from the temporary lock position, a force may be applied to cap 118 directed away from the needle, to separate the needle hub 114c from the projections 214a.

In one embodiment, needle hub 114c is connected to shield 104 using a coupling member 122, which has a living hinge 124 located thereon. In another embodiment, as previously discussed, needle hub 114c is unitarily formed with the coupling member. As shown in FIG. 2A, coupling member 122 is located at the proximal end 206 and is generally aligned at an angle to cap 118 with living hinge 124 integrally formed thereon. Living hinge 124 allows rotation of cap 118 relative to base 114. In one embodiment, living hinge is formed with sufficient material thickness as to create a natural outward bias for maintaining the cap in an extended position during use (FIG. 1). To couple cap 118 to needle 112, coupling member 122 may be integrated directly with needle hub 114c upon mounting needle 112, as previously discussed with respect to a unitary embodiment. Alternatively, coupling member 122 may be separately formed and subsequently attached to needle hub 114c, which has needle 112 attached thereto. Cap 118 of shield 104 may be mounted to needle hub 114c at the time of assembly or packaging of shield 104 so that a package may include not only the shield 104 but also the needle hub 114c having the needle 112 attached thereto. The coupling member 122 may be attached to the needle hub 114c in a number of known methods, such as by providing an opening on the coupling so that the opening grabs the needle hub in an interference fit. Alternatively or in addition thereto, detents, chemical bonding, or adhesive bonding may be used to attach the two. In yet another embodiment, shield 104 may be packaged without a needle and needle hub. During use, shield 104, and more particularly the opening on the coupling, may be slid over the needle hub. In one operational embodiment, shield 104 is configured to pivot (rotate) about hinge mechanism 124 to move away from needle 112 along the direction indicated by arrow 126 (FIG. 1). As described in detail below, shield 104 may be pivoted, again along the direction indicated by arrow 126, to substantially envelop needle 112 within recessed space 208.

Referring again to FIGS. 2A and 2B, cap 118 includes an integral push lever 212 extending from base wall 208a outside from recessed space 208. In one exemplary embodiment, push lever 212 includes a distally facing surface 212a, which is generally a horizontal surface disposed perpendicular to the longitudinal axis of cap 118 and dimensioned to generally accept a user's finger. Push lever 212 also includes a tapered side surface 212b, which is generally an angled surface relative to the longitudinal axis of cap 118 and dimensioned to generally conform to the side of a user's finger. The user may use push lever 212 to apply a compressive axial force on surface 212a toward a proximal end of cap 118, which causes cap 118 to rotate with respect to base 114. One of ordinary skill in the art will appreciate that application of a compressive force to surface 212b causes cap 118 to rotate in the opposite direction, i.e., a clockwise momentum viewing from the perspective of FIG. 1. Other configurations of a push lever may be used within the spirit and scope of aspects of the present invention. Additionally, a user may simply grab the two side walls 208b, 208c to exert both an axial force and a radial force to open or close cap 118.

Referring to FIG. 2A, cap 118 is generally configured to receive plug 120 in a telescoping arrangement through passageway 202a. Plug 120 may be inserted through passageway 202a into recessed space 208 to capture needle 112 to place shield 104 in the secured position (FIG. 5B).

Figure 3A:
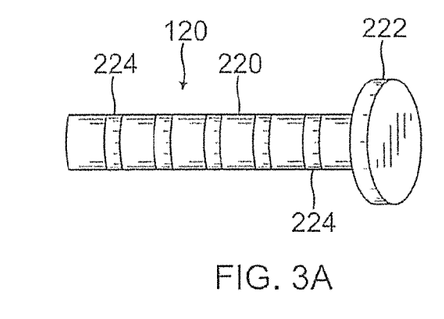
FIGS. 3A and 3B are a simplified side view and axial view, respectively, of a plug for use in the protective shield in accordance with an embodiment of the present invention.
Figure 3B:
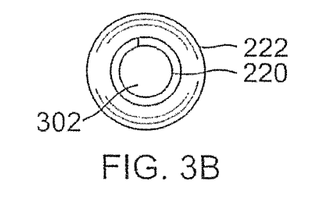

As shown in FIGS. 3A and 3B, plug 120 has a tubular shaped body 220 defining a hollow interior 302. Plug 120 is closed at the distal end and may be capped by, for example, a button 222. In one exemplary embodiment, button 222 includes a distally facing surface, which is generally a horizontal surface disposed perpendicular to the longitudinal axis of plug 120 and dimensioned to generally accept a user's finger or a portion of the user's palm. As shown in FIG. 3B, the proximal end of plug 120 is open to provide access to hollow interior 302 of tubular body 220. Plug 120 may be made of any suitable material, such as hard plastic, that is substantially impervious to penetration by sharp objects, such as needle 112. Generally, the outer diameter of tubular body 220 is made to "fit" the diameter of passageway 202a. This arrangement allows tubular body 220 to be slip fit into recessed space 208 of cap 118. The fit between passageway 202a and plug 120 may have a slight interference or friction fit. The slight interference fit acts to keep tubular body 220 from prematurely passing through passageway 202a and entering into recessed space 208, until a compressive force substantial enough to overcome the friction of the slight interference fit is purposely applied to button 222.

Figure 4:
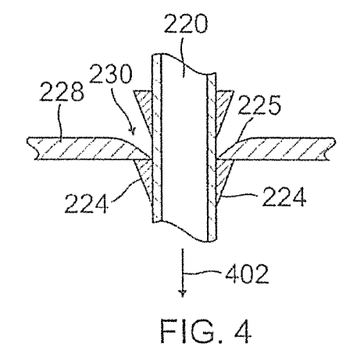
FIG. 4 is a simplified sectional view of the ratchet operation of the protective shield in accordance with an embodiment of the present invention.

In one embodiment, tubular body 220 may include a rack of teeth 224 made to engage a pawl to allow linear motion of plug 120 in only one direction through passageway 202a, while preventing motion in the opposite direction. In one exemplary embodiment, as shown in FIG. 4, an edge 225 formed in or inserted along the diameter of passageway 202a, may be angled to act as a pawl 228 to engage teeth 224. In this embodiment, when teeth 224 are moving in one direction (arrow 402), pawl 228 slides up and over each tooth 224 in turn, with the inherent spring of the edge material forcing pawl 228 back into a depression 230 before the next tooth 224. If an attempt is made to move tubular body 220 in the opposite direction, the angle of pawl 228 causes it to catch against tooth 224 and stop further motion in that direction. Alternatively, teeth 224 may be formed of a resilient material, such that teeth 224 are squeezed past pawl 228 with the inherent spring of the tooth material forcing teeth 224 to spring back under the pawl 228 to oppose movement in the reverse direction.

Thus, a protective shield for covering a needle having a sharp tip is provided which includes a cap defining a recessed space along a lengthwise axis. The cap is pivotable from a first position aligned with a longitudinal centerline of a needle occupying a portion of the recessed space and a second position non-aligned with the longitudinal centerline of the needle. A passageway is defined through two spaced apart end plates formed at the distal end of the cap.

In another aspect of the invention, a plug comprising an open proximal end, a closed distal end and a hollow interior body therebetween is provided. The plug is movably insertable into a recessed space of a cap. The plug is displaceable with respect to the cap through the passageway to capture, within the hollow tubular body of the plug and through the open end, the needle occupying the portion of the recessed space. The tubular body may also include a rack of exterior teeth configured to engage with the cap to restrict the displacement of the tubular body to a single direction relative to the cap. The plug is insertable into the recessed space of the cap through the open axial end formed on the two spaced apart end plates which connect to the two side walls of the cap. The closed distal end of the plug comprises an enlarged flange having a planar exterior surface opposite the open end and adapted to be urged by a user to manually displace the plug.

The operation of the hinged cap assembly will now be described with reference to FIGS. 5A and 5B and with further reference to FIG. 1. As shown in FIG. 1, arrow 126 indicates that cap 118 is capable of rotating radially outwardly relative to needle axis 130 to expose needle 112. In this open position, an injection may be performed or fluid may be drawn into the syringe without shield 104 interfering with needle 112. In one alternative embodiment, cap 118 incorporates a catch (not shown) to mate with a corresponding catch (not shown) disposed on needle hub 114c to keep the cap in an open position relative to the needle.

With reference to FIG. 5A, shield 104 is shown in a packaged or ready position. Shield 104 may be packaged in the configuration shown inside a vacuum pack enclosure having, for example, a peelable cover configured for peeling to remove the assembly from the package. To place shield 104 in the packaged or ready position, cap 118 is rotated radially inwardly relative to needle axis 130 causing living hinge 124 to operate to facilitate the rotation. Once fully rotated, cap 118 comes into longitudinal alignment with needle 112, needle hub 114c engages with retaining means 214 and at least a portion of needle 112 extends into recessed space 208 through first needle alignment member 210a. In some embodiments, it may be desirable to maintain shield 104 in the ready position shown in FIG. 5A, for example, while transporting syringe 102 to the patient before actual use. Once syringe 102 is ready to be used, the retaining force applied by retaining means 214 to needle hub 114c may be overcome and cap 118 may be rotated away from needle 112.

Referring now to FIG. 5B, once needle 112 has been used, for example, once a patient has been injected and the needle is contaminated, shield 104 is transformable from the ready position to a secured position. As shown in 5B, needle 112 positioned within recessed space 208 may be "capped" by encapsulating at least a portion of needle 112 within hollow interior 302 (FIG. 3B) of plug 120.

Operationally, a healthcare provider may apply a compressive force on button 222 of plug 120 to create axial movement of plug 120 relative to cap 118. At least a portion of tubular body 220 is urged or pressed through passageway 202a and into recessed space 208. As hollow, tubular body 220 enters into recessed space 208, needle 112, which occupies the recessed space in the ready position, is made to enter into hollow interior 302 defined by tubular body 220 to encapsulate or trap at least a portion of needle 112.

As tubular body 220 is made to pass through passageway 202a, teeth 224 disposed on the surface of tubular body 220 are urged past pawl 228 (FIG. 4). In this way, movement of plug 120 is limited to a single direction, thereby, prohibiting plug 120 from moving in a reverse direction or being "pulled" out from recessed space 208. This ensures that once needle 112 is encapsulated into tubular body 220, needle 112 may not be re-exposed. Additionally, shield 104 may not be rotated radially away from the longitudinal axis of needle 112 to expose the needle.

Figure 6:
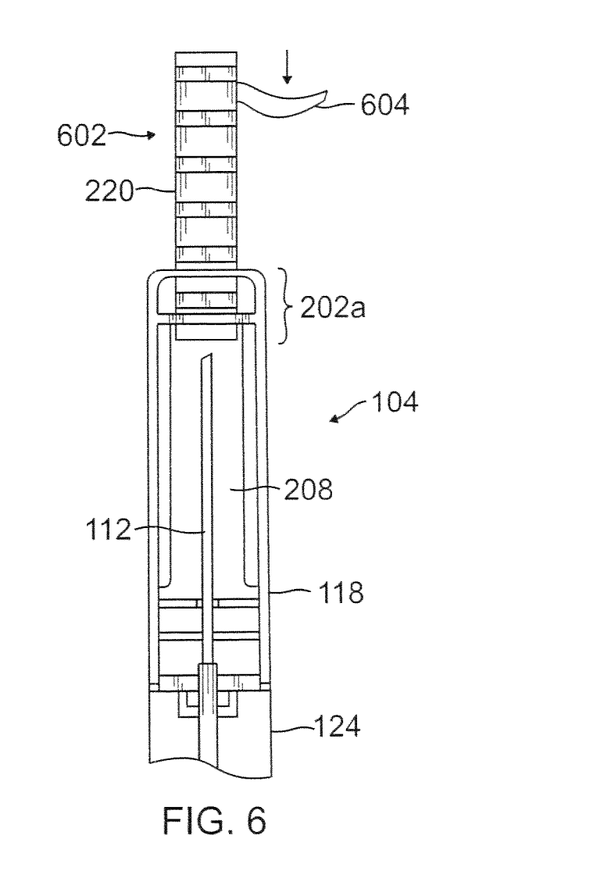
FIG. 6 is a simplified sectional view of an alternative embodiment of the protective shield in accordance with the present invention.

With reference now to FIG. 6, another exemplary embodiment of a plug 602 for use with cap 118 is shown. The shield 104 operates as described with reference to other embodiments. However, in this embodiment, plug 602 incorporates an integral lever 604 extending horizontally from tubular member 220 away from the longitudinal axis ("off-axis") of plug 602.

In one exemplary embodiment, lever 604 includes a distally-facing surface, which may be generally arc-shaped and dimensioned to generally conform to the side of a user's finger. As such, the healthcare provider may use lever 604 to apply a compressive axial force toward a proximal end of cap 118. One of ordinary skill in the art will appreciate that other configurations of a lever may be used within the spirit and scope of aspects of the present invention. In one embodiment, lever 604 may be positioned on the side of tubular body 220 that is to the side or opposite hinge 124. Thus, any torque created on shield 104 by depressing lever 604 that may otherwise cause cap 118 to rotate away from needle 112 is restrained by hinge 124.

Although embodiments and their components have been specifically described and illustrated, many modifications, combinations, and variations of the embodiments will be apparent to those skilled in the art. Furthermore, it is understood and contemplated that features specifically discussed for one embodiment may be adopted for inclusion with another embodiment provided the functions are compatible. Accordingly, it is to be understood that shield and components thereof constructed according to principles of this invention may be embodied other than as specifically described herein. The invention is also defined in the following claims.

What is claimed is:

1. A protective shield for covering a needle, comprising:
a coupling member;
a cap defining a recessed space extending between a first end and a second end along a lengthwise axis, the cap being hinged at the first end to the coupling member and pivotable relative to the coupling member between a first position aligned with a longitudinal centerline of a needle occupying a portion of the recessed space and a second position non-aligned with the longitudinal centerline of the needle; and
a plug at the second end of the cap and having a plug portion extending away from the second end, said plug being slidable along the lengthwise axis of the cap from the second end of the cap to the first end of the cap so as to cover the needle occupying the portion of the recessed space;
wherein the plug comprises a hollow tubular body having an open end, and the tubular body comprises a rack of teeth configured to engage a pawl to restrict the displacement of the tubular body to a single direction.

2. The protective shield of claim 1, wherein the cap is hinged to the coupling member with a living hinge.

3. The protective shield of claim 1, further comprising a push lever extending outwardly from the cap, the push lever including a surface adapted to receive a compressive force to manually displace the cap.

4. The protective shield of claim 1, further comprising a retaining means for retaining the needle within the recessed space when the cap is in the first position.

5. The protective shield of claim 1, wherein the recessed space comprises an internal clearance configured to allow the needle to pass unobstructed when the cap is in the first position.

6. The protective shield of claim 1, wherein the plug includes a closed end having a planar exterior surface opposite the open end and adapted to be urged by a user to manually displace the tubular body.

7. The protective shield of claim 1, wherein the plug includes a lever offset with respect to a longitudinal centerline of the plug positioned opposite the open end and adapted to be urged by a user to manually displace the tubular body.

8. A protective shield comprising:
a cap defining a recessed space extending along a lengthwise axis between a first end of the cap and a second end of the cap, and a coupling member at the first end of the cap and configured for connecting the first end of the cap to a syringe having a needle, the cap being movable at the coupling member between an open position where the recessed space is not occupied by the needle, and a ready position where the needle occupies a portion of the recessed space; and
a plug located at the second end of the cap and displaceable along the lengthwise axis toward the first end of the cap to a secured position to capture the needle inside the recessed space when the cap is in the ready position;
wherein the plug comprises a hollow tubular body including an open end, and the tubular body comprises a rack of teeth configured to engage a pawl to restrict the displacement of the tubular body to a single direction.

9. The protective shield of claim 8, wherein the cap is hinged to the coupling member with a living hinge.

10. The protective shield of claim 8, further comprising a push lever extending outwardly from the cap, the push lever including a surface adapted to receive a compressive force to manually displace the cap.

11. The protective shield of claim 8, wherein the recessed space comprises an internal clearance to allow the needle to pass unobstructed when the cap is displaced to the ready position.

12. The protective shield of claim 8, wherein the plug includes a button positioned opposite an open end and adapted to be urged by a user to manually displace the tubular body.

13. The protective shield of claim 8, wherein the plug defines a longitudinal center line, and wherein the plug includes a lever offset with respect to the longitudinal centerline of the plug positioned opposite an open end and adapted to be urged by a user to manually displace the tubular body.

14. A protective shield comprising:
a cap defining a recessed space between a first end and a second end;
a coupling member connecting the first end of the cap to a syringe having a needle, the cap being displaceable between an open position in which the recessed space is not occupied by the needle, and a ready position in which the needle occupies a portion of the recessed space; and
a plug having a tubular body and an open end, the plug being displaceable within the cap from the second end of the cap toward the first end of the cap to a secured position in which the plug is located to receive the needle through the open end of the plug when the cap is in the ready position, wherein the tubular body comprises a rack of teeth configured to engage a pawl in the cap so as to limit the displacement of the plug to a single direction.

* * * * *

UNITED STATES PATENT AND TRADEMARK OFFICE
CERTIFICATE OF CORRECTION

PATENT NO. : 8,888,742 B2
APPLICATION NO. : 13/129799
DATED : November 18, 2014
INVENTOR(S) : Volker Harms et al.

Page 1 of 1

It is certified that error appears in the above-identified patent and that said Letters Patent is hereby corrected as shown below:

In the Specification

In column 4, line 51, delete "202b." and insert -- 202b, --, therefor.

Signed and Sealed this
Fourteenth Day of July, 2015

Michelle K. Lee
*Director of the United States Patent and Trademark Office*